United States Patent [19]

Frank

[11] 4,204,072
[45] May 20, 1980

[54] TRIS(N-CARBALKOXYLAMINOMETHYL)-PHOSPHINES

[75] Inventor: Arlen W. Frank, Slidell, La.

[73] Assignee: The United States of America as represented by the Secretary of Agriculture, Washington, D.C.

[21] Appl. No.: 964,751

[22] Filed: Nov. 29, 1978

[51] Int. Cl.$^2$ .................... C07C 125/06; D06M 13/44
[52] U.S. Cl. ........................................ 560/158; 8/183; 8/185; 8/187; 560/148
[58] Field of Search ......................................... 560/158

[56] References Cited
FOREIGN PATENT DOCUMENTS
938367 10/1963 United Kingdom ..................... 560/158

Primary Examiner—Norman Morgenstern
Assistant Examiner—Michael Shipper
Attorney, Agent, or Firm—M. Howard Silverstein; David G. McConnell; Raymond C. Von Bodungen

[57] ABSTRACT

The title compounds, having the formula $(RO_2CNHCH_2)_3P$, are prepared by reacting a quaternary phosphonium salt, having the formula $(RO_2CNHCH_2)_4P^+X^-$, with a base, preferably one that is capable of reacting with and thereby inactivating the by-product formaldehyde or formaldehyde derivative. The products are useful as intermediates for the preparation of finishing agents that impart flame retardant properties to cotton fabrics.

8 Claims, No Drawings

TRIS(N-CARBALKOXYLAMINOMETHYL)PHOSPHINES

CROSS REFERENCE TO RELATED APPLICATIONS:

Ser. No. 964,852—"TRIS(N-CARBALKOXYLAMINOMETHYL)PHOSPHINE OXIDES AND SULFIDES".

Ser. No. 964,853—"QUATERNARY PHOSPHONIUM SALTS BEARING CARBAMATE GROUPS".

BACKGROUND OF THE INVENTION (1) Field of the Invention

This invention relates to novel tris(N-carbalkoxylaminomethyl)phosphines, and to methods for preparing the same.

(2) Description of the Prior Art

Tertiary phosphines which are characterized by having a carbamate group attached to each of the phosphorus substituents through their nitrogen atom have not been heretofore known in the art.

Furthermore, methods describing preparation of such compounds from the corresponding quaternary phosphonium salts, and the consequences of using formaldehyde-reactive bases for this purpose, have not been previously known.

SUMMARY AND OBJECTS OF THE INVENTION

The instant invention discloses as new compounds tris(N-carbalkoxylaminomethyl)phosphines and methods for preparing the same.

The principal object of the invention is to prepare novel tris(N-carbalkoxylaminomethyl)phosphines from tetrakis(N-carbalkoxylaminomethyl)phosphonium salts by reaction with a base.

It is another object of the instant invention to provide a method of preparing novel tris(N-carbalkoxyaminomethyl)phosphines which are substantially free of by-products.

Other objects and improvements of the invention will become obvious from the description of the preferred embodiments.

DESCRIPTION OF THE PREFERRED EMBODIMENTS

The novel compounds of this invention have the general formula $(RO_2CNHCH_2)_3P$, where R is an alkyl or substituted alkyl radical having from 1 to 6 carbon atoms.

In accordance with the practice of this invention, the new compounds are prepared by reacting a tetrakis(N-carbalkoxylaminomethyl)phosphonium salt having the general formula $(RO_2CNHCH_2)_4P^+X^-$, where R is as defined above and X is an inorganic acid radical, with a base capable of forming a salt with the inorganic acid HX, and recovering the product from the resulting reaction mixture.

The tetrakis(N-carbalkoxylaminomethyl)phosphonium salts, themselves novel substances, are prepared by condensing an alkyl carbamate having the general formula $RO_2CNH_2$, where R is as defined above, with a tetrakis(hydroxymethyl)phosphonium salt having the general formula $(HOCH_2)_4P^+X^-$, where X is as defined above, in a molar ratio of at least 4:1. Examples of such substances are phosphonium salts in which R is methyl, ethyl, isopropyl, 2-methoxyethyl, n-butyl, and the like, and in which X is chloride, iodide, sulfate, and the like (Examples 17–26).

The bases employed in the practice of this invention comprise those substances capable of forming a salt with the acid HX, encompassing both inorganic and organic substances. The inorganic bases are exemplified by sodium hydroxide, barium hydroxide, sodium bicarbonate, disodium phosphate, trisodium phosphate, sodium sulfite, ammonium hydroxide, and the like. The organic bases are exemplified by triethylamine, morpholine, and the like. For reasons that are explained below, some of these bases, both inorganic and organic, are preferred to others.

The reaction between the tetrakis(N-carbalkoxylaminomethyl)phosphonium salt and the base is most conveniently carried out in the presence of a solvent such as water or ethanol, but may also be performed in the absence of a solvent. The molar ratio may be varied from 3:1 to 1:20, the preferred ratio being from 1:1 to 1:2. The temperature may be varied from 0° to 150° C., depending on the strength of the base and the physical properties of the solvent. The pressure may be atmospheric, subatmospheric, or higher than atmospheric. If the product is air-sensitive, as is often the case with tertiary phosphines, the reaction may be carried out in an atmosphere of an inert gas, such as nitrogen or argon.

The hydrolysis of quaternary phosphonium salts to tertiary phosphines or their oxides by means of alkali is well known; see for example L. Maier, "Organic Phosphorus Compounds", G. M. Kosolapoff and L. Maier, eds., Wiley-Interscience, New York, 1972, Vol. 1, pp. 49–54. When this reaction is applied to tetrakis(N-carbalkoxylaminomethyl)phosphonium salts, however, the product is a mixture of tertiary phosphines containing little or none of the desired tris(N-carbalkoxylaminomethyl)phosphine. For example, the hydrolysis of tetrakis(N-carbomethoxylaminomethyl)phosphonium chloride ($R=CH_3$, $X=Cl$ in the formula above), hereinafter referred to as TMPC, with aqueous sodium hydroxide gives the desired product, tris(N-carbomethoxylaminomethyl)phosphine, hereinafter referred to as TMP, as a water-insoluble solid in yields of 0 to 29%, depending on the reaction conditions (Table I). The major product is a water-soluble, liquid tertiary phosphine which cannot be induced to yield any TMP after work-up (nor any of the crystalline oxide, TMPO, after oxidation). Barium hydroxide gives a 21% yield of TMP. Other moderately strong bases, such as sodium bicarbonate, disodium phosphate, trisodium phosphate or triethylamine, give yields in the 40 to 60% range, as does sodium hydroxide buffered with borax or phosphate. Yields of 87 to 92%, approaching the quantitative, are only attained with bases that are capable of reacting with formaldehyde (or formaldehyde derivatives), such as ammonium hydroxide, morpholine or sodium sulfate (Table I).

I suggest, without wishing to be bound by any specific hypothesis, that the preferred bases function by trapping the by-product alkyl N-methylenecarbamate, $RO_2CN=CH_2$, which is released in the hydrolysis of the phosphonium salt. Such a by-product is expected to be highly reactive, and capable of reacting either with the product, giving an N-substituted tertiary phosphine, or with water, giving an alkyl N-hydroxymethylcarbamate, $RO_2CNHCH_2OH$. The preferred bases could react directly with the alkyl N-methylenecarbamate giving products of the type N(CH$_2$NHCO$_2$R)$_3$ or RO$_2$CNHCH$_2$SO$_3$Na, or they could abstract formaldehyde from the alkyl N-hydroxymethylcarbamate giving products such as hexamethylenetetramine or the bisulfite addition compound of formaldehyde. In either event, the result would be the inactivation of the by-product, enabling the product to be recovered without hindrance.

TABLE I

HYDROLYSIS OF TMPC WITH VARIOUS BASES

| Example | Base | Conditions | TMP (% yield) |
|---|---|---|---|
| 1 | NaOH | 100° C., 15 min | 29.1[a] |
| 2 | NaOH (borax) | " | 42.7 |
| 3 | NaOH (Na$_2$HPO$_4$) | " | 43.7 |
| 4 | " | 60° C., 90 min[b] | 45.0 |
| 5 | Ba(OH)$_2$[c] | 100° C., 1 hr | 21.0 |
| 6 | NaHCO$_3$ | " | 60.1[d] |
| 7 | Na$_2$HPO$_4$ | " | 60.3 |
| 8 | Na$_3$PO$_4$[c] | 100° C., 30 min | 48.2 |
| 9 | Triethylamine | " | 53.4 |
| 10 | " | 25° C., 3 hr | 54.1[e] |
| 11 | Morpholine | 100° C., 1 hr | 46.7 |
| 12 | " | 25° C., 2 hr | 90.6[f] |
| 13 | NH$_4$OH | " | 87.0 |
| 14 | Na$_2$SO$_3$ | 100° C., 1 hr | 92.5 |

[a]Yield raised to 51.3% by subsequent treatment with ammonium hydroxide (Example 15).
[b]Sodium hydroxide solution added dropwise to the buffered TMPC solution during the first 45 min.
[c]Mixture yellowed when the amount of base was doubled.
[d]Subsequent treatment with 6N HCl regenerated only 24.4% of the TMPC.
[e]Yield unaffected by subsequent treatment with ammonium hydroxide or sodium bisulfite.
[f]Together with 93.5% yield of morpholine hydrochloride, mp 175°–176° C. (lit. mp 175°–176° C.)

The preferred bases are seen to fall into two categories. In the first category are substances which contain hydrogen attached to nitrogen, i.e. ammonia, primary, and secondary (but not tertiary) amines. When using bases in this category, an excess of the base should be employed to ensure that there is a sufficient quantity to react with both the by-product and the acid HX. The preferred molar ratio is therefore 1:2 or higher.

In the second category is sodium sulfite. When this base reacts with the acid HX, the base is transformed into sodium bisulfite, which is known to react with formaldehyde to give a crystalline adduct (J. F. Walker, "Formaldehyde", 3rd ed., Reinhold Publishing Corp., 1964, p. 251). In this case, no excess of base is necessary, and the preferred molar ratio is therefore 1:1.

Other categories will no doubt suggest themselves, to those skilled in the art, from among the many types of compounds that are capable of reacting with formaldehyde or formaldehyde derivatives (Walker, op. cit.).

The novel tris(N-carbalkoxylaminomethyl)phosphines of this invention were found to be useful as intermediates for the preparation of novel tris(N-carbalkoxylaminomethyl)phosphine oxides and sulfides.

The procedures are illustrated in Examples 27–29. Examples 30–33 illustrate procedures for preparing the phosphine oxides and sulfides directly from the phosphonium salts without pausing to isolate the tri(N-carbalkoxylaminomethyl)phosphines of this invention. A comparison of Examples 30 and 33 shows that the effect of preferred vs. non-preferred bases is transmitted through the oxidation step, for the products are different.

Carbamates are employed extensively in the textile industry to impart durable press properties to cotton fabrics (H. F. Mark, N.S. Wooding and S. M. Altas, "Chemical Aftertreatment of Textiles", Wiley-Interscience, New York, 1971, pp 417–64). Some attempts have been made to incorporate phosphorus in these finishes to also impart flame retardant properties to the cotton fabrics, without notable success (W. A. Reeves and R. M. Perkins, Colourage Annual 1 [1971]).

The novel tris(N-carbalkoxylaminomethyl)phosphine oxides and sulfides prepared from the products of this invention each contain nitrogen and phosphorus, the two elements that are considered necessary and sufficient for imparting flame retardant properties to cotton fabric. The elements, moreover, are in the ratio of 3 parts nitrogen to 1 part phosphorus that is considered to be optimum for flame retardant efficiency, and the phosphorus is in a form that needs no further stabilization.

For practical purposes, it is also desirable that the flame retardant finish be durable to laundering. To this end, methods are given for chemical binding the novel compounds to the cotton cellulose through the use of crosslinking agents such as formaldehyde. Examples 34–39 illustrate the application of TMPO to cotton printcloth, with formaldehyde as the binding agent. The TMPO is first methylolated, and is then caused to react with the cotton cellulose by curing at an elevated temperature in the presence of a catalyst. The catalyst, it may be noted, can be either an acid or a base. Example 40 illustrates the application of this finish to cotton sateen. Examples 41–45 illustrate the application of TMPO to cotton printcloth with urea, melamine or their methylol derivatives as co-reactants.

The flammability of the treated fabric was determined by the Oxygen Index (O.I.) Test, as described in the "Annual Book of ASTM Standards", American Society for Testing and Materials, Philadelphia, 1974, Part 35, p. 732, or by the Match Test, as described by W. A. Reeves and G. L. Drake, Jr., "Flame Resistant Cotton", Merrow, Watford Herts., England, 1971, p. 14. Wrinkle recovery (WRA, W+F, conditioned) was determined by the Monsanto test, as described in the "Annual Book of ASTM Standards", op. cit., Part 32, p. 226.

Phosphorus analyses were performed by the X-ray fluorescence method, nitrogen analyses by the Kjeldahl method, and formaldehyde analyses by the chromotropic acid method after digestion with sulfuric acid.

EXAMPLE 1

A slurry of 20.94 g (0.05 mol) of TMPC in 50 ml of water was treated dropwise, under a slow flow to argon gas, with a solution of 2.00 g (0.05 mol) of sodium hydroxide in 25 ml of water. During the addition, which took 15 min, the mixture cleared, turned milky, and cleared again. After heating at 100° C. for 15 min to complete the reaction, the solution, pH 8.4 and strongly positive to an iodine test for P(III), abruptly crystallized, giving 4.30 g (29.1% yield) of TMP, mp 82°–102° C. (sealed tube), identified by comparison of its infrared spectrum with that of the product of Example 13. The filtrate was extracted with chloroform, giving 16.49 g (65% yield) of a different tertiary phosphine, isolated as a colorless, neutral oil, n$_D^{20}$ 1.5011, soluble in water, acetone and chloroform. IR (neat): 775m, 860w br, 1010m, 1055w, 1145s, 1190s, 1250vs, 1530vs (NH, amide II), 1710vs (C=O, amide I), and 3350 m br cm$^{-1}$.

EXAMPLES 2 TO 4

Reaction of TMPC with sodium hydroxide in the presence of 0.01 mol of a buffer, following Example 1, gave crystalline TMP in 43 to 45% yield. The results are given in Table I, where the buffer is listed in brackets.

EXAMPLES 5 TO 12

Reactions of TMPC with various other bases are summarized in Table I. The procedure of Example 1 was followed in each experiment, using 0.05 mol of base unless otherwise stated. The yield of crystalline TMP varied from 40 to 60%.

EXAMPLE 13

Conc. ammonium hydroxide (10 ml) was added to a well-stirred slurry of 20.94 g (0.05 mol) of TMPC in 50 ml of water in an apparatus previously purged with argon. There was no exotherm nor gassing, but the mixture gradually thickened. After 30 min, more water (50 ml) was added to facilitate stirring. The mixture was then stirred for 2 hr, filtered, and the filter cake washed with water and dried in a vacuum desiccator, giving 12.85 g (87.0% yield) of TMP as a white, crystalline powder, mp 100°–125° C. All of these operations were performed under argon, for the product becomes hot and sticky when exposed to air. One recrystallization from 2-propanol raised the mp (sealed tube) to 137°–140° C. IR (Nujol): 768w, 777w, 848m, 962w, 1005m, 1140s, 1190m, 1235s, 1255vs, 1290s, 1420m, 1535vs br (NH, amide II), 1700vs and 1735s (C=O, amide I), and 3350m (NH) cm$^{-1}$. TMP is soluble is ethanol, chloroform and acetone, and insoluble in water, ether, carbon tetrachoride and benzene. It can be recrystallized from water (8 ml/g) or 2-propanol (7 ml/g).

EXAMPLE 14

A slurry of 20.94 g (0.05 mol) of TMPC in 50 ml of water was treated with 12.60 g (0.10 mol) of sodium sulfite, purged with argon, and heated at 100° C. for 1 hr, cooled and filtered, giving 13.66 g (92.5% yield) of crystalline TMP, mp 113°–119° C.

EXAMPLE 15

TMPC was hydrolyzed with sodium hydroxide as described in Example 1. After the completion of the reaction, the mixture was treated, without filtering, with 10 ml of conc. ammonium hydroxide and stirred overnight under argon. The yield of TMP, mp 107°–117° C., was 7.57 g (51.3%), consequently higher than in Example 1 but lower than in Example 13.

EXAMPLE 16

A solution of 400.0 g (0.464 mol) of octakis(N-carbomethoxylaminomethyl)diphosphonium sulfate, [(CH$_3$O$_2$CNHCH$_2$)$_4$P$^+$]$_2$SO$_4$=, in 500 ml of water was purged with argon and treated with 200 ml of conc. ammonium hydroxide over a 15 min period at 21° to 26° C. Solids started to separate within minutes, and after 2 hr another 200 ml of water was added to facilitate stirring. After 4 hr, the product was collected on a filter, rinsed with water and dried, giving 280.0 g (102% yield) of crystalline TMP, mp 110°–115° C.

EXAMPLE 17

This example illustrates the preparation of TMPC from tetrakis(hydroxymethyl)phosphonium chloride, (HOCH$_2$)$_4$P$^+$Cl$^-$, hereinafter referred to as THPC.

A mixture of 47.64 g (0.25 mol) of THPC, 75.07 g (1.00 mol) of methyl carbamate and 200 ml of toluene was heated to reflux in an apparatus fitted with a Dean-Stark trap for azeotropic removal of the water. The mixture was held at reflux until the evolution of water ceased; after 2.5 hr, 18.5 ml (1.03 ml) had been collected. The product crystallized on standing to a hard mass and was broken up, triturated under ethyl acetate, filtered, and dried, giving 90.67 g (86.5% yield) of TMPC, mp 177° C. d. Two recrystallizations from ethanol afforded pure TMPC as a white, crystalline solid, mp 189° C. d. IR (Nujol) 770 m, 787w, 850m, 855m,sh, 865 m, 966w, 1005m, 1020m 1160m, 1265 vs, 1300s, 1540vs (NH, amide II), 1700s and 1740vs (C=O, amide I; doublet in Nujol but a singlet, 1730vs, in DMSO), 3220m (NH bonded), and 3300m (NH free) cm$^{-1}$. $^1$H NMR (DMSO-d$_6$) δ 3.63 s, 12H, CH$_3$), 4.32 (t, 8H, CH$_2$, J=5.0 Hz, collapsing with D$_2$O to d, J=4.0 Hz), and 8.05 (m, ~4H, NH, vanishing with D$_2$O). $^{31}$P NMR (DMSO) δ −30.7.

Anal. Calcd for C$_{12}$H$_{24}$ClN$_4$O$_8$P: C, 34.41; H, 5.78; Cl, 8.47; N, 13.38; P, 7.40; mol. wt., 419. Found: C, 34.64; H, 5.66; Cl, 8.71; N, 13.24; P, 7.53; mol. wt. (osmometric in H$_2$O), 249, 259.

TMPC is partially soluble in water, DMSO (7 ml/g) and methanol, and insoluble in other common organic solvents. Its aqueous solution is mildly acidic (pH 4.5). It can be recrystallized from ethanol (20 ml/g) or 2-propanol (75 ml/g), and is air stable, nonhygroscopic and odorless.

EXAMPLE 18

A 5 liter flask was charged with 1191 g (5 mol) of 80% aqueous THPC and 750 g (10 mol) of methyl carbamate, heated briefly to 100° C., allowed to cool to 65° C., charged with another 750 g of methyl carbamate, and heated at gentle reflux (110° C.) for 3 hr. Next day, the crystalline mass was broken up, triturated in portions with ethanol, filtered, and allowed to air dry in evaporating dishes. The product, TMPC, was a white, crystalline solid, 1472 g, mp 189° C. d (70.3% yield). Workup of the mother liquor raised the yield to 80.1%.

EXAMPLE 19

Reaction of THPC (47.64 g, 0.25 mol) with 89.10 g (1.00 mol) of ethyl carbamate [Caution: carcinogenic], following Example 17, gave 71.53 g (60.2% yield) of tetrakis(N-carbethoxylaminomethyl)phosphonium chloride, (C$_2$H$_5$O$_2$CNHCH$_2$)$_4$P$^+$Cl$^-$, as a white, crystalline solid, mp 112°–113° C., after two recrystallizations from ethyl acetate. IR (Nujol) 772w, 782w, 850w, 860w, 1020m, 1085w, 1145m, 1170m, 1215m, 1230m,sh, 1260vs, 1280s, 1300s, 1515vs and 1535s (NH, amide II), 1680s and 1730s (C=O, amide I; doublet in Nujol or conc. KBr, changing to singlet in CHCl$_3$, or dil. KBr), 3230m (NH bonded), and 3360w (NH free) cm$^{-1}$. $^1$H NMR (CDCl$_3$) δ 1.26 (t, 12H, CH$_3$, J=7.0 Hz) 4.17 (q, CH$_2$C, J=7.0 Hz), 4.42 (m, PCH$_2$, collapsing with D$_2$O to d, δ 4.46, J=3.0 Hz; total CH$_2$, 16H), and 7.43 (m, NH, vanishing with D$_2$O). −P NMR (DMSO) δ −31.2

Anal. Calcd. for C$_{16}$H$_{32}$ClN$_4$O$_8$P: C, 40.46; H, 6.79; Cl, 7.47; N, 11.80; P, 6.52. Found: C, 40.49; H, 6.80; Cl, 7.59; N, 11.60; P, 6.61.

The product is soluble in water, ethanol, chloroform, benzene, DMSO (1.5 ml/g) and acetone, and insoluble in ether, carbon tetrachloride and cyclohexane. Its aqueous solution is mildly acidic. It is readily recrystallized from ethyl acetate (5 ml/g), but tends to oil out from hot carbon tetrachloride or toluene.

EXAMPLE 20

Reaction of 9.53 g (0.05 mol) of THPC with 20.62 g (0.20 mol) of isopropyl carbamate, following Example 17 but using ether instead of ethyl acetate, gave 9.32 g (45.6% yield) of tetrakis(N-carbisopropoxylaminomethyl)phosphonium chloride, [(CH$_3$)$_2$CHO$_2$CNHCH$_2$]$_4$P+Cl−, as a white, crystalline solid, mp 140°–141° C., after two recrystallizations from water. IR (Nujol) 772w, 832w, 875w, 884w, 925w, 934w, 1005m, 1015m, 1110s, 1145m, 1175m, 1250vs, 1280m, 1300m, 1510s (NH, amide II), 1720s, 1730vs (C=O, amide I), 3220m (NH bonded), and 3320m (NH free) cm−1. 1H NMR (CDCl$_3$) δ 1.27 (d, 24H, CH$_3$, J=6.0 Hz), 4.44 (br s, CH$_2$, resolved with D$_2$O to d, δ 4.46, J=3.0 Hz), 4.94 (m, CH, J=6.0 Hz; combined CH$_2$ and CH, 12H), and 7.31 (m, 4H, NH, vanishing with D$_2$O).

Anal. Calcd. for C$_{20}$H$_{40}$ClN$_4$O$_8$P: C, 45.24; H, 7.59; Cl, 6.68; N, 10.55; P, 5.83. Found: C, 45.11; H, 7.37; Cl, 6.63; N, 10.74; P, 5.94.

The product is soluble in ethanol, chloroform, carbon tetrachloride and benzene, and insoluble in ether. It can be recrystallized from ethyl acetate (10 ml/g) or water (3 ml/g).

EXAMPLE 21

Reaction of 9.53 g (0.05 mol) of THPC with 29.29 g (0.25 mol) of n-butyl carbamate, following Example 17, gave 37.67 g of a colorless oil that partly crystallized on standing. Attempts to separate the excess n-butyl carbamate from the product by extraction with hot ligroin, ether, or carbon tetrachloride were unsuccessful, for the two substances exhibit the same solubility behavior. Half of the mixture was therefore dissolved in ethanol (25 ml) and percolated through 50 g of Bio-Rad AG 50W-X4 cation exchange resin, using ethanol as the eluent. The neutral fractions yielded 17.6 mmol (70.4% yield) of HCl, 3.10 g (21.2% recovery) of n-butyl carbamate, and 2.24 g (14.6% yield) of di-n-butyl N,N'-methylenedicarbamate, mp 93°–95° C. (identified by comparison of its IR, NMR and mp with an authentic sample, mp 97°–98° C.). The phosphonium salt fractions, eluted with ethanolic HCl, yielded 7.83 g of a viscous, colorless oil, n$_D^{20}$ 1.4839, whose composition, determined by NMR and elemental analysis, comprised some unreacted THPC (11.2% yield) in addition to the product (38.4% yield). To remove the unreacted THPC, the oil was taken up in chloroform (50 ml), extracted twice with water, filtered, stripped and dried, giving 4.71 g (30.1% yield) of tetrakis(N-carbo-n-butoxylaminomethyl)phosphonium chloride, (C$_4$H$_9$O$_2$CNHCH$_2$)$_4$P+Cl−, as a viscous, colorless oil, n$_D^{20}$ 1.4951. IR (Nujol) 1515vs (NH, amide II), 1710vs (C=O, amide I) and 3230s (NH) cm−1. 1H NMR (CDCl$_3$) δ 0.94 (t, 12H, CH$_3$, J=6.0 Hz), 1.1–2.0 (m, 16H, CH$_2$C), 4.13 (t, 8H, OCH$_2$, J=6.0 Hz), 4.43 (m, 8H, PCH$_2$) and 7.37 (m, 4H, NH, vanishing slowly with D$_2$O). 31P NMR (CHCl$_3$) δ −30.0.

The product is soluble in all of the common organic solvents, including toluene and hot ligroin, and insoluble in water.

EXAMPLE 22

Reaction of 9.53 g (0.05 mol) of THPC with 35.74 g (0.30 mol) of 2-methoxyethyl carbamate, following Example 17, gave 40.71 g of a viscous, almost colorless oil that resisted efforts at crystallization or conversion to a crystalline oxalate or picrate. Half of the oil was therefore dissolved in 10 ml of water and precolated through the ion exchange resin described in Example 21, using water as the eluent. The neutral fractions yielded 16.9 mmol (67.6% yield) of HCl. The phosphonium salt fractions yielded 11.10 g of oil which was taken up in chloroform, filtered, stripped and dried (omitting the extraction with water, since the partition is unfavorable), giving 9.05 g (53.7% yield) of tetrakis[N-carbo(2-methoxyethoxy)aminomethyl]phosphonium chloride, (CH$_3$OCH$_2$CH$_2$O$_2$CNHCH$_2$)$_4$P+Cl−, as a viscous, colorless oil, n$_D^{20}$ 1.5094. IR (neat) 1515s (NH, amide II), 1720vs (C=O, amide I) and 3240m (NH) cm1. 1H NMR (CDCl$_3$) δ 3.38 (s, 12H, CH$_3$), 3.61 (m, 8H, 2-CH$_2$), 4.29 (m, 8H, 1-CH$_2$), 4.53 (m, 8H, PCH$_2$), and 7.42 (m, ~4H, NH, vanishing slowly with D$_2$O). −P NMR (CHCl$_3$) δ −31.0.

The phosphonium salt is soluble in water, ethanol, acetone, chloroform, ethyl acetate and hot toluene.

EXAMPLE 23

A mixture of 270.8 g (0.5 mol) of 75% tetrakis(hydroxymethyl)phosphonium sulfate and 300.2 g (4.0 mol) of methyl carbamate was heated to reflux with constant stirring, held at 100° to 108° C. for 2 hr, allowed to cool, and then stripped of water under reduced pressure, giving 443.8 g (102.9% yield) of octakis(N-carbomethoxylaminomethyl)diphosphonium sulfate, [(CH$_3$O$_2$CNHCH$_2$)$_4$P]$_2$++SO$_4$=, as an almost colorless, tacky glass. IR (KBr) 1720 vs (C=O, amide I), 1515vs (NH, amide II) and 3300 s (NH) cm−1. −P NMR (H$_2$O) δ −28.8.

EXAMPLE 24

A solution of 2.08 g (0.01 mol) of barium chloride in 25 ml of water was mixed with a solution of 8.88 g (0.01 mol) of the product of Example 23 in 25 ml of water, causing an immediate separation of solids. The mixture was heated to boiling to coagulate the solids, allowed to cool and filtered, giving 2.31 g (99.0% yield) of barium sulfate. The filtrate, stripped under vacuum, left a crystalline residue which was rinsed with ethanol, giving 5.62 g (67.1% yield) of TMPC, mp 187.5°–188° C. d, identical to the product of Example 17.

EXAMPLE 25

TMPC (8.38 g, 0.02 mol) was added to a solution of sodium iodide (3.00 g, 0.02 mol) in 30 ml of ethanol, heated at reflux for 1 hr, cooled, and filtered, giving 3.23 g of granular solid consisting of sodium chloride and unreacted TMPC. The latter was removed by stirring with DMSO, leaving 0.67 g (57.3% yield) of sodium chloride. The ethanol filtrate was stripped, taken up in hot chloroform, filtered to remove unreacted sodium iodide (0.22 g, giving a positive test with acidified iodate), and stripped again. The residue (8.45 g) was recrystallized from ethanol, giving 5.01 g (49.1% yield) of tetrakis(N-carbomethoxylaminomethyl)phosphonium iodide, (CH$_3$O$_2$CNHCH$_2$)$_4$P+I−, as a white, crystalline solid, mp 142.5°–143° C. IR (Nujol) 768m, 784w, 848m, 860m, 963w, 1005m, 1020m, 1150m, 1185m,br, 1205m, 1260vs, 1295s, 1535vs (NH, amide II), 1690s and 1730vs (C=O, amide I), 3230m (NH, bonded) and 3300m,sh (NH free) cm−1. 1H NMR (DMSO-d$_6$) δ 3.67 (s, 12H, CH$_3$), 4.33 (t, 8H, CH$_2$, J=5.0 Hz, collapsing with D$_2$O to d, J=4.0 Hz), and 7.67 (m, 4H, NH, vanishing with D$_2$O). 31P NMR (DMSO) δ −30.3.

Anal. Calcd. for $C_{12}H_{24}IN_4O_8P$: I, 24.87; P, 6.07. Found: I, 24.50 (gravimetric), 25.05 (by iodometric titration); P, 6.12.

EXAMPLE 26

A solution of 8.38 g (0.02 mol) of TMPC in 200 ml of methanol was percolated through the ion exchange resin described in Example 21. It was necessary to wrap the column in heating tape and warm it to 40°–50° C. to prevent the salts from crystallizing. The column was eluted with hydrogen bromide in methanol, yielding four liquid fractions (6.79 g) followed by eight solid fractions (19.19 g). The solids were combined, shaken with ethanol, and filtered, giving 6.50 g (70.2% yield) of tetrakis (N-carbomethoxylaminomethyl)phosphonium bromide, $(CH_3O_2CNHCH_2)_4P^+Br^-$, mp 180°–184° C. d. One recrystallization from ethanol (75 ml/g) afforded the pure salt as a white, crystalline solid, mp 185°–186° C. d, suffering no loss in weight when heated in a drying pistol for 2 hr at 100° C./0.5 mm. IR (Nujol) 770m, 786w, 847m, 863m, 965w, 1005m, 1020m, 1160m, 1185m, 1210m, 1235s,sh, 1260vs, 1300s, 1370m, 1550vs (NH, amide II), 1700s and 1730vs (C=O, amide I), 3220s (NH bonded) and 3320m (NH free) cm$^{-1}$. $^1$H (DMSO-d$_6$) δ 3.65 (s, 12H, CH$_3$), 4.35 (t, 8H, CH$_2$, J=5.0 Hz, collapsing with D$_2$O to d, J=4.0 Hz), and 7.75 (br t, 4H, NH, vanishing with D$_2$O). $^{31}$P NMR (DMSO) δ −30.0.

Anal. Calcd for $C_{12}H_{24}BrN_4O_8P$: Br, 17.25; P, 6.69. Found: Br, 17.71; P, 6.93.

EXAMPLE 27

This example illustrates the preparation of TMPO from TMP.

A 30% solution of hydrogen peroxide (57.0 g, 0.5 mol) was added dropwise to a vigorously stirred slurry of 147.6 g (0.5 mol) of TMP in 500 ml of acetone under an argon atmosphere. Ice-bath cooling was applied as necessary to counter the strongly exothermic reaction. The TMP gradually dissolved, and was all in solution when two-thirds of the peroxide had been added. About 10 min. after the addition was completed, the product started to crystallize. Next day, the solid was collected on a filter, washed with acetone and dried, giving 98.9 g (63.5% yield) of TMPO, mp 179°–180° C. Work-up of the filtrate raised the yield to 126.0 g (81.0% yield). Two recrystallizations from ethanol afforded pure TMPO as a white, crystalline solid, mp 189°–190° C. IR (Nujol): 780m, 830w, 852m, 972w, 1015m, 1135m, 1145m, 1160m, 1190m, 1260s, 1300m, 1540s (NH, amide II), 1710vs br (C=O, amide I), 3250 w (NH, bonded) and 3400w (NH, free) cm$^{-1}$. $^1$H NMR (DMSO-d$_6$): δ 3.60 (s, CH$_3$), 3.47 (t, CH$_2$, J=9.0 Hz, blending into the CH$_3$ peak with D$_2$O; combined CH$_3$ and CH$_2$, 15H), and 7.34 (m, 3H, NH, vanishing with D$_2$O) ppm.

Anal. Calcd for $C_9H_{18}N_3O_7P$: C, 34.73; H, 5.83; N, 13.50; P, 9.95. Found: C, 34.69; H, 5.70; N, 13.48; P, 10.00.

The phosphine oxide TMPO is soluble in chloroform and insoluble in water, acetone, and the common organic solvents. It can be recrystallized from ethanol (25 ml/g) or water. When heated above its melting point, it gasses without discoloration and froths to a tan-colored resin at 260° C.

EXAMPLE 28

Hydrogen peroxide (30%) was added dropwise to a well-stirred slurry of 1476.2 g (5 mols) of TMP in 2000 ml of water under an argon atmosphere, with ice-bath cooling applied as needed to maintain the reaction temperature between 20° and 30° C. The addition was stopped after 3.5 hr, when 550.6 g (4.85 mols) of 30% hydrogen peroxide had been added. At this point, an iodine test for unreacted TMP was negative, and the product, which had separated during the reaction, abruptly foamed to the surface. The product was collected on a filter, rinsed with water and air-dried, giving 826.6 g (53.1% yield) of crystalline TMPO, mp 179°–180° C.

EXAMPLE 29

This example illustrates the preparation of tris(N-carbomethoxylaminomethyl)phosphine sulfide, $(CH_3O_2CNHCH_2)_3PS$, hereinafter referred to as TMPS, from TMP.

A mixture of 2.95 g (0.01 mol) of TMP, 0.32 g (0.01 g-atom) of sulfur and 25 ml of benzene was heated to reflux under an argon atmosphere. After 1 hr. most of the solids had dissolved. The mixture was cooled and stripped of benzene under reduced pressure. The residue was taken up in hot acetone, filtered hot to remove the unreacted sulfur (0.12 g), and stripped again under reduced pressure, leaving 2.40 g (73.4% yield) of TMPS as a white, crystalline solid. Two recrystallizations from ethanol afforded pure TMPS, mp 136.5°–137° C. IR (Nujol): 772w, 780w, 790w, 810w, 846m,sh, 855s, 970m, 1015s br, 1145s, 1190s, 1240vs, 1290vs, 1520vs br (NH, amide II), 1710vs and 1740s (C=O, amide I), and 3400s (NH) cm$^{-1}$. $^1$H NMR (DMSO-d$_6$):δ3.61 (s, CH$_3$), 3.72 (t, CH$_2$, J=3.0 Hz, collapsing with D$_2$O to d, J=3.0 Hz; combined CH$_3$ and CH$_2$, 15H), and 7.39 (m, 3H, NH, vanishing with D$_2$O) ppm. $^{31}$P NMR (DMSO): δ48.5 ppm.

Anal. Calcd. for $C_9H_{18}N_3O_6PS$: C, 33.03, H, 5.54; N, 12.84; P, 9.46; S, 9.80. Found: C, 33.08; H, 5.49; N, 12.82; P, 9.60; S, 9.80.

The phosphine sulfide TMPS is soluble in chloroform, and insoluble in water or ethanol. It can be recrystallized from ethanol (6 ml/g), 2-propanol or water.

EXAMPLE 30

This example and the two which follow illustrate the use of a preferred base, ammonium hydroxide, in the preparation of TMPO or TMPS from TMPC or octakis(N-carbomethoxylaminomethyl)diphosphonium sulfate, $[(CH_3O_2CNHCH_2)_4P]_2SO_4$.

Conc. ammonium hydroxide (10 ml) was added to a well-stirred slurry of 20.94 g (0.05 mol) of TMPC (see Example 18) in 100 ml of water in an apparatus previously purged with argon. The mixture gradually thickened. After 2 hr. the mixture, still containing the excess base and the by-products, was treated dropwise with 5.67 g (0.05 mol) of 30% hydrogen peroxide over a 20 min. period, with ice-bath cooling applied as needed to keep the temperature below 30° C. Next day, the mixture was stripped to dryness in a rotary evaporator, triturated with ethanol and filtered, giving 13.69 g (88.0% yield) of crystalline TMPO, mp 176°–178° C.

TMPC is not oxidized by hydrogen peroxide in the absence of a base.

EXAMPLE 31

An identical experiment in which the excess base and by-products were removed prior to oxidation gave 13.91 g (89.4% yield) of crystalline TMPO, mp 174°–177° C.

EXAMPLE 32

Conc. ammonium hydroxide (500 ml) was added to a solution of 1078.4 g (1.25 mol) of octakis(N-carbomethoxylaminomethyl)diphosphonium sulfate (see Example 23) in 1500 ml of water in an apparatus previously purged with argon. TMP started to separate within minutes. After 2 hr. the mixture, still containing the excess base and the by-products, was treated dropwise with 977 g (2.87 mol) of 20% ammonium sulfide over a 2 hr. period at 25°–30° C. Next day, the product was collected on a filter, rinsed throughly with water and air-dried, giving 521.4 g of crude TMPS, mp 120°–125° C. One recrystallization from ethanol gave 398.3 g (48.9% yield) of crystalline TMPS, mp 132°–135° C.

EXAMPLE 33

This example illustrates the effect of using a base—sodium hydroxide, which is not one of the preferred bases—on the preparation of TMPO from TMPC.

A slurry of 20.94 g (0.05 mol) of TMPC in 50 ml of water was treated dropwise with a solution of 2.00 g (0.05 mol) of sodium hydroxide in 25 ml of water. During the addition, which took 5 min, the mixture cleared, turned milky, and cleared again. After 15 min, the solution was extracted with chloroform, and the chloroform extract filtered and stripped. The residue (16.79 g), a viscous, colorless oil which, unlike TMP, could not be induced to crystallize, was dissolved in 100 ml of acetone and treated dropwise with 5.70 g (0.05 mol) of 30% hydrogen peroxide over a 5 min period. The temperature rose to 40° C., and at the end an iodine test for unreacted tertiary phosphine was negative. The solution was stripped of acetone in a rotary evaporator, taken up in chloroform, extracted with water to remove any remaining peroxide, filtered, and stripped again, giving 14.00 g (62% yield) of the tertiary phosphine oxide as a colorless oil, $n_D^{20}$ 1.4962. IR (neat): 775w, 1005w br, 1055w, 1150m, 1190m, 1250s,1290m sh, 1530s (NH, amide II), 1710vs (C=O, amide I), and 3350m (NH) cm$^{-1}$. $^1$H NMR (CDCL$_3$): δ3.7–3.9 (m, 12H, CH$_3$), 3.9–4.6 (m, 8H, PCH$_2$), 6.63 (m, 2H, NH), and 8.13 (m, 1H, NH) ppm. $^{31}$P NMR (CHCl$_3$): δ45.3 ppm. The elemental analyses (N, 10.82; P, 5.98) clearly showed a 4:1 molar ratio of nitrogen to phosphorus, as opposed to 3:1 in TMPO.

The product was soluble in water, ethanol, acetone and chloroform, and insoluble in ether, carbon tetrachloride, ethyl acetate and benzene.

EXAMPLE 34–39

These examples illustrate the application of TMPO to cotton fabric with formaldehyde as the binding agent.

In each case, the padding formulation was prepared by dissolving 13.07 g (42 mmol) of TMPO in a solution of 0.20 g of sodium hydroxide in 10.23 g (126 mmol) of 37% formalin, neutralizing to pH 7 with 6 N HCl, adding 12.5 mmol of the catalyst and 0.1 g of Triton X-100 (a wetting agent), and making up to 50 g with water. The final pH of each formulation is given in the table.

An 80×80 desized, scoured and bleached cotton printcloth was cut into 6"×12" swatches, immersed in one of the formulations, padded to about 95% wet pickup, dried at 85° C. for 4 min in a forced draft oven, and cured at 160° C. for 4 min in another forced-draft oven. The swatches were then rinsed for 15 min in hot running tap water and line dried. The results for a series of such experiments with various catalysts are assembled in Table II.

TABLE II

| Example | Catalyst | pH | % Add-on | % P | % N | % CH$_2$O | O.I. | WRA |
|---|---|---|---|---|---|---|---|---|
| 34 | MgCl$_2$/citric acid | 2.3 | 10.0 | 1.07 | 1.16 | 2.76 | 0.211$^a$ | 280 |
| 35 | Zn(NO$_3$)$_2$ | 5.5 | 8.4 | 0.86 | 0.92 | 1.34 | 0.210$^a$ | 252 |
| 36 | MgCl$_2$ | 6.5 | 1.5 | 0.08 | 0.13 | 0.09 | 0.183 | 207 |
| 37 | None | 7.0 | 1.0 | 0 | 1.01 | 0.17 | 0.179 | 194 |
| 38 | Na$_2$CO$_3$ | 10.7 | 6.1 | 0.73 | 0.73 | 0.06 | 0.214 | 192 |
| 38$^b$ | Na$_2$CO$_3$ | 10.7 | 9.0 | 1.05 | 1.21 |  | 0.234 | 212 |
| 39 | NaOH | 11.8 | 4.3 | 0.62 | 0.62 | 0.01 | 0.204 | 192 |

$^a$Match test angle 80°.
$^b$Cured 10 min at 160°.

The add-on was negligible in the absence of a catalyst (Example 37), but increased to 5 to 10% when either an acid or a base catalyst was added to the formulation. Sodium carbonate (Example 38) and magnesium chloride/citric acid (Example 34) gave comparable add-ons, provided that the cure time for the former was extended to 10 min. Magnesium chloride by itself (Example 36) was not sufficiently acidic to be an effective catalyst. The flame resistance (O.I.) and wrinkle resistance (WRA) both increased with add-on when the catalyst was an acid, but only the flame resistnace increased when the catalyst was a base.

EXAMPLE 40

Application of the methylolated TMPO formulation to cotton sateen with magnesium chloride/citric acid catalyst, as described in Example 34, gave fabric with an 11.6% add-on and a 90° match test angle. These results were similar to those obtained with the printcloth.

EXAMPLES 41–45

These examples illustrate the application of TMPO to cotton fabric with urea or melamine as co-reactants, and formaldehyde as the binding agent.

In each case, the padding formulation (50 g) contained 13.07 g (42 mmol) of TMPO, 84 mmol of the co-reactant, 12.5 mmol of catalyst and 0.1 g of Triton X-100. In all but Example 42, the TMPO was methylolated with 10.23 g (126 mmol) of 37% formalin prior to addition of the coreactant. In Examples 42 and 43, 10.07 g (84 mmol) of crystalline N, N'-dimethylolurea was substituted for the urea, and in Example 45, 5.30 g (42 mmol) of melamine was substituted for the urea. The composition and final pH of each formulation are given in Table III.

TABLE III

| Ex. | catalyst | TMPO methylolated | Urea methylolated | ph | % Add-on | % P | % N | Match angle |
|---|---|---|---|---|---|---|---|---|
| 41 | NaH$_2$PO$_4$ | Yes | No | 4.7 | 12.2 | 0.32 | 3.05 | 20 |
| 42 | MgCl$_2$ | No | Yes | 5.6 | 11.3 | 0.24 | 2.72 | 20 |

TABLE III-continued

| Ex. | catalyst | TMPO methylolated | Urea methylolated | ph | % Add-on | % P | % N | Match angle |
|---|---|---|---|---|---|---|---|---|
| 43 | NaH$_2$PO$_4$ | Yes | Yes | 4.9 | 35.0 | 1.50 | 4.68 | 110 |
| 44 | MgCl$_2$ | Yes | No | 6.6 | 5.8 | 0.17 | 1.04 | 0 |
| 45 | MgCl$_2$ | Yes | No$^a$ | 6.7 | 34.4 | 0.92 | 7.75 | 80 |

$^a$Melamine

With magnesium chloride as the catalyst, melamine helped to bind the methylolated TMPO to the fabric (Example 45), but urea did not (Example 44). Sodium dihydrogen phosphate, a mildly acidic catalyst, was too acidic for use with melamine, but helped urea to bind the methylolated TMPO to the fabric, especially when both the urea and the TMPO were methylolated prior to padding (Example 43). The fabrics with the highest add-on passed the match test with an angle of 110°.

The foregoing examples are given merely for purposes of illustration, and should not be construed as limiting the scope of the invention.

I claim:

1. A tris(N-carbalkoxylaminomethyl)phosphine compound having the formula (RO$_2$CNHCH$_2$)$_3$P, where R is an alkyl radical having from 1 to 6 carbon atoms.

2. The compound of claim 1 wherein the compound is tris(N-carbomethoxylaminomethyl)phosphine.

3. A process for preparing a tris(N-carbalkoxylaminomethyl)phosphine which comprises reacting a tetrakis(N-carbalkoxylaminomethyl)phosphonium salt having the formula (RO$_2$CNHCH$_2$)$_4$P$^+$X$^-$, where R is an alkyl radical having from 1 to 6 carbon atoms and X is an inorganic acid radical, with a base capable of forming a salt with the inorganic acid HX, and recovering the product from the resulting reaction mixture.

4. The process of claim 3 wherein X is a chloride.

5. The process of claim 3 wherein X is a sulfate.

6. The process of claim 3 wherein the base is a substance capable of reacting with and thereby inactivating a by-product selected from formaldehyde and a formaldehyde derivative of an alkyl carbamate having the formula RO$_2$CNH$_2$, where R is similarly defined.

7. The process of claim 6 wherein the base is a substance which contains hydrogen attached to nitrogen, selected from the group consisting of ammonia, primary amines, and secondary amines.

8. The process of claim 6 wherein the base is sodium sulfite.

* * * * *